US006806293B1

(12) United States Patent
Zamir

(10) Patent No.: US 6,806,293 B1
(45) Date of Patent: Oct. 19, 2004

(54) USE OF PHEROMONE COMPOUNDS HAVING MAP KINASE MODULATING ACTIVITY

(75) Inventor: Nadav Zamir, Holon (IL)

(73) Assignee: Darley Pharmaceuticals LTD, Tel Aviv (IL)

( * ) Notice: Subject to any disclaimer, the term of this patent is extended or adjusted under 35 U.S.C. 154(b) by 118 days.

(21) Appl. No.: 09/804,209

(22) Filed: Mar. 12, 2001

(51) Int. Cl.$^7$ .................. A61K 31/045; A61K 31/22
(52) U.S. Cl. .................. 514/738; 514/739; 514/546
(58) Field of Search ................ 514/738, 739, 514/546

(56) References Cited

U.S. PATENT DOCUMENTS

| | | | |
|---|---|---|---|
| 2,900,756 A | | 8/1959 | Jacobson |
| 5,190,978 A | | 3/1993 | Nakamura et al. |
| 5,405,941 A | * | 4/1995 | Johnson ................ 530/350 |
| 5,525,625 A | * | 6/1996 | Bridges et al. ............ 514/456 |
| 5,633,392 A | * | 5/1997 | Berliner et al. ............ 552/530 |
| 5,728,376 A | * | 3/1998 | Attygalle et al. ............ 424/84 |
| 5,846,778 A | | 12/1998 | Hawkins et al. ............ 435/69.1 |
| 5,922,699 A | * | 7/1999 | Jennings-White et al. .. 514/170 |
| 5,958,721 A | | 9/1999 | Marshall et al. ............ 435/29 |
| 6,165,461 A | | 12/2000 | Cobb et al. ............ 424/94.5 |

FOREIGN PATENT DOCUMENTS

| | | | |
|---|---|---|---|
| EP | 0 896 819 A | | 2/1999 |
| WO | WO 97/27845 | | 8/1997 |
| WO | WO 00/50600 | * | 8/2000 |

OTHER PUBLICATIONS

W.S. Leal et al., "Medicinal Alkaloid As A Sex Pheromone", Nature, vol. 385, Jan. 1997, p. 213.

Camm AJ and Yap YG, "What Should We Expect From The Next Generation Of Antiarrhythmic Drugs!", J. Cardiovasc Electrophysiol Feb. 1999, pp. 307–317.

Danty E, Cornuet JM and Masson C, "Honeybees Have Putative Olfactory Receptor Proteins Similar To Those Of Vertebrates", C.R. Acad Sci III Dec. 1994, p. 1073.

Ishii K and Murad F, "ANP Relaxes Bovine Tracheal Smooth Muscle And Increases cGMP", Am J Physiol Mar. 1989, C495–500.

Nahcshon S, Zamir O, Matsuda Y and Zamir N, "Effects Of ANP Receptor Antogonists On ANP Secretion From Adult Rat Cultured Atrial Myocytes", Am J Physiol Mar. 1995, E.428–432.

Nikaido H, "Multiple Antibiotic Resistance And Efflux", Curr Opin Microbiol Oct. 1998, pp. 516–523.

Noula c, Constantinou V, Nicolaou A, Gibbons WA and Kokotos G, "Lipid Mimetics As Inhibitors Of Human Platelet Phospholipase A2", Biochem Soc Trans May 1996, 303s.

Roberts GD, Goodman NL, Heifets L, Larsh HW, Lindner TH, McClatchy JK, McGinnis MR, Siddiqi SH and Wright P, "Evaluation Of The BACTEC Radiometric Method For Recovery Of Mycobacteria And Drug Susceptibility Testing Of Mycobacterium Tuberculosis From Acid–Fast Smear–Positive Specimens", J Clin Microbiol Sep. 1983, pp. 689–696.

van Veen HW, Callaghan R, Soceneantu L, Sardini A, Konings WN and Higgins CF, "A Bacterial Antibiotic–Resistance Gene That Complements The Human Multidrug–Resistance P–Glycoprotein Gene", Nature Jan. 1998, vol. 15, pp. 291–295.

Irene Bosch and James Croop, "P–Glycoprotein Multidrug Resistance And Cancer", Biochimica et al Biophysica Acta, 1288 (1996), pp. F37–F54.

Michael Chinkers, David L. Garbers, Ming–Shi Chang, David G. Lowe, Hemin Chin, David V. Goeddel and Stephanie Schulz, "A Membrane Form Of Guanylate Cyclase Is An Atrial Natriuretic Peptide Receptor", Nature, vol. 338, Mar. 2, 1989, pp. 78–83.

Joelle Cohen–Tannoudji, J. Einhorn and J.P. Signoret, "Ram Sexual Pheromone: First Approach Of Chemical Identification", Physiology & Behavior, 1994 vol. 56, No. 5, pp. 955–961.

Ke–Hong Ding, Nawab Ali and Ata A. Abdel–Latif, "Atrial Natriuretic Peptide Provokes A Dynamic Increase In Cyclic GMP Formation And Markedley Inhibits Muscarinic–Stimulated $Ca^{2+}$Mobilisation In SV–40 Transformed Cat Iris Sphincter Smooth Muscle (SV–CISM–2) Cells", Cell. Signal. vol. 11, No. 2, 1999, pp. 87–94.

Ke–Hong Ding, Andrew J. Latimer and Ata A. Abdel–Latif, "Activation Of Particulate Guanylyl Cyclase By Endothelins In Cultured SV–40 Transformed CAT IRIS Sphincter Smooth Muscle Cells", Life Sciences, vol. 64, No. 3, 1999, pp. 161–174.

Hans–Jurgen Fulle, Robert Vassar, David C. Foster, Ruey–Bing Yang, Richard Axel and David L. Garbers, "A Receptor Guanylyl Cyclase Expressed Specifically In Olfactory Sensory Neurons", Proc. Natl. Acad. Sci. USA, vol. 92, Apr. 1995, pp. 3571–3575.

M.R. Hardeman, P.T. Goedhart, J.G.G. Dobbe and K.P Lettinga, "Laser–Assisted Optical rotational Cell Analyser (L.O.R.C.A.), I. A New Instrument For Measurement Of Various Structural Hemorheological Parameters", Clinical Hemorheology, vol. 14, No. 4, 1994, pp. 605–618.

(List continued on next page.)

Primary Examiner—Zohkeh Fay
Assistant Examiner—Brian-Yong S. Kwon
(74) Attorney, Agent, or Firm—Watov & Kipnes, P.C.

(57) ABSTRACT

A method of screening pheromone compounds for mitogen-activated protein (MAP) kinase modulating activity and for employing such pheromone compounds in compositions suitable for the prevention or treatment of diseases, conditions, and symptoms thereof benefitting from modulation of MAP kinase activity.

6 Claims, No Drawings

OTHER PUBLICATIONS

M.R. Hardeman, P.T. Goedhart and N.H. Schut, "Laser–Assisted Optical Rotational Cell Analyser (L.O.R.C.A.); II Red Blood Cell Deformability: Elongation Index Versus Cell Transit Time", Clinical Hemorheology, vol. 14, No. 4, 1994, pp. 619–630.

Adrian J. Hobbs, Annie Higgs and Salvador Moncada, "Inhibiton Of Nitric Oxide Synthase As A Potential Therapeutic Target", Annu. Rev. Pharmacol. Toxicol., 1999, pp. 191–220.

Kentaro Horikawa, Hideki Nakakuma, Shoichi Nagakura, Makoto Kawakita, Tadashi Kagimoto, Masao Iwamori, Yoshitaka Nagai, Tsukasa Abe and Kiyoshi Takatsuki, "Hemolysis Of Human Erythrocytes Is A New Bioactivity Of Gangliosides", J. Exp. Med., vol. 174, Dec. 1991, pp. 1385–1391.

Dawn M. Juilfs, Hans–Jurgen Fulle, Allan Z. Zhao, Miles D. Houslay, David L. Garbers and Joseph A. Beavo, "A Subset Of Olfactory Neurons That Selectivity Express cGMP–Stimulated Phosphodiesterase (PDE2) And Guanylyl Cyclase–D Define A Unique Olfactory Signal Tansduction Pathway", Proc. Natl. Acad. Sci. USA, vol. 94, Apr. 1997, pp. 3388–3395.

David R. Kelly, "When Is A butterfly Like An Elephant?", Chemistry & Biology, Aug. 1996, pp. 595–602.

Walter Soares Leal, Paulo H.G. Zarbin, Hubert Wojtasek, Shigefumi Kuwahara, Makoto Hasegawa and Yasuo Ueda, "Medicinal Alkoloid As A Sex Pheromone", Nature, vol. 385, Jan. 16, 1997, p. 213.

Nobuhiko Miwa, Shingo Nakkamura, Norio nagao, Sensuke Naruse, Yukiharu Sato and Katsuhiro Kageyama, "Cyctotoxicity To Tumors By ∞, β–Dihydric Long–Chain Fatty Alcohols Isolated From Esterolysates Of Uncytotoxic Sheep Cutaneous Wax: The Dependence On The Molecular Hydrophobicity Balance Of N—Or Iso–Alkyl Moiety Bulkiness And Two Hydroxyl Groups", Cancer Biochem. Biophys., 1997, vol. 15, pp. 221–233.

L.E.L. Rasmussen, Terry D. Lee, Wendell L. Roelofs, Aijun Zhang and G. Doyle Daves, Jr., "Insect Pheromone In Elephants", Nature, vol. 379, Feb. 22, 1996, p. 684.

Fred E. Regnier and John H. Law, "Insect Pheromones", Journal Of Lipid Research, vol. 9, 1968, pp. 541–551.

Joel G. Hardman, Lee E. Limbird, Perry B. Molinoff, Raymond W. Ruddon and Alfred Goodman Gilman, "The Phamacological Basis Of Therapeutics", Goodman & Gilman's, Ninth Edition, International Edition, 1996, pp. 839–874.

Wendell L. Roelofs, "Chemistry Of Sex Attraction", Proc. Natl. Acad. Sci. USA, vol. 92, Jan. 1995, pp. 44–49.

Pieter Sonneveld, MD and Erik Wiemer, MD, "Inhibitors Of Multidrug Resistance", 1997, Current Opinion in Oncology, vol. 9, pp. 543–548.

MJA Walker, MJ Curtis, DJ Hearse, RWF Campbell, MJ Janse, DM Yellon, SM Cobbe, Sj Coker, JB Harness, DWG Harron, AJ Higgins, DG Julian, MJ Lab., AS Manning, BJ Northover, JR Parratt, RA Riemersma, E Riva, DC Russell, DJ Sheridan, E Winslow and B Woodard, "The Lambeth Conventions: Guidlines For The Study Of Arrhythmias In Ischaemia, Infarction, and Reperfusion", Cardiovascular Research, 1988, pp. 447–455.

Nadav Zamir, Rivka Riven–Kreitman, Mira Manor, Amnon Makler, Shmaryahu Blumbert, Dina Ralt and Michael Eisenbach, "Atrial Natriuretic Peptide Attracts Human Spermatozoa In Vitro", Biochemical And Biophysical Research Communications, vol. 197, No. 1, Nov. 30, 1993, pp. 116–122.

Nadav Zamir, Shmuel Tuvia, Rivka Riven–Kreitman, Shlomo Levin and Rafi Korenstein, "Atrial Natriuretic Peptide: Direct Effects On Human Red Blood Cell Dynamics", Biochemical And Biophysical Research Communications, vol. 188, No. 3, Nov. 16, 1992, pp. 1003–1009.

Bei Zhang, Gino Salituro, Deborah Szalkowski, Zhihua Li, Yan Zhang, Immaculada Royo, Dolores Vilella, Maria Teresa Diez, Fernando Pelaez, Caroline Rudy, Richard L. Kendall, Xianzhi Mao, Patrick Griffin, Jimmyu Calaycay, Juleen r. Zierath, James V. Heck, Roy G. Smith and David E. Moller, "Discovery Of A Small Molecule Insulin Mimetic With Antidiabetic Activity In Mice", Science, vol. 284, May 7, 1999, pp. 974–977.

G. Ziegelberger, MJ van den Berg, K–E Kaissling, S Klumpp and JE Schultz, "Cyclic GMP Levels And Guanylate Cyclase Activity In Pheromone–Sensitive Antennae Of The Silkmoths Antheraea Polyphemus And Bombyx Mori", The Journal Of Neuroscience, vol. 10, Apr. 1990, pp. 1217–1225.

* cited by examiner

USE OF PHEROMONE COMPOUNDS HAVING MAP KINASE MODULATING ACTIVITY

FIELD OF THE INVENTION

The present invention is generally directed to compounds having mitogen-activated protein kinase modulating activity, and to methods of screening such compounds and to compositions employing the same. Modulation of mitogen-activated kinase activity has been associated with the treatment of a variety of medical diseases, conditions, and/or symptoms thereof in warm-blooded animals including humans.

BACKGROUND OF THE INVENTION

Intercellular communication is essential for the development and normal function of all multicellular organisms. Cells communicate and respond to extracellular signals by utilizing various cellular mechanisms called signal transduction pathways. These pathways involve a series of molecular events culminating in the activation of effector mechanisms that result in specific cellular responses. Certain disturbances in signal transduction pathways are involved in the pathogenesis of various diseases, conditions and symptoms thereof including cancer, cardiovascular disease, inflammation, autoimmune diseases (e.g. rheumatoid arthritis), neurodegenerative diseases (e.g. Alzheimer's disease), and other diseases including acquired immune deficiency syndrome (AIDS) and the like.

One of the important signal transduction pathways is the mitogen-activated protein (MAP) kinase pathway. This pathway is essential in cellular growth and differentiation. It is known that blockage of the MAP kinase pathway suppresses tumor growth. In this signal transduction cascade, sequential activation of kinases and subsequent protein phosphorylation lead to the activation of transcription factors at the DNA level.

The sequential activation of kinases (also known as the protein kinase cascades) is a common mechanism of signal transduction in many cellular processes. Mitogen-activated protein kinases are believed to include up to five levels of protein kinases that sequentially activate each other through the process of phosphorylation. Among several mechanisms for activating these cascades, one is believed to be initiated by a small GTP binding protein which transmits the signal to the protein kinases. The signal is then transmitted down the cascade by enzymes at the various levels. The existence of multiple levels in each of the MAP kinase cascades is believed essential for signal amplification, specificity and tight regulation of the transmitted signals.

Nicholas S. Duesbery et al., *Nature Medicine*, Vol. 5/7 (July, 1999) report that tumor cells proliferate and spread throughout the body in apparent disregard of normal environmental cues. The inhibition of the mitogen-activated protein kinase signal transduction pathway enables tumor cells to revertto a non-transformed phenotype and bypass the arrest of tumor growth in the body. It is also known that many oncogenes activate the mitogen-activated protein kinase signal transduction pathway and it is this inappropriate activation that mediates the transformed phenotype.

The pathophysiology of many diseases involves dysfunctional intercellular signaling. As indicated above, in cancer, for example, some oncogenes encode signal transduction pathway proteins involved in the regulation of self proliferation. Expression of these oncogenes may induce chronic activation that results in uncontrolled proliferation. Thus, tumor cells are effectively released from normal regulation and thereby proliferate, enabling the tumor to enlarge. In conditions manifesting unstable angina and myocardial infarction, platelets aggregate and participate in the occlusion of coronary arteries by responding to a variety of signals released by the rupture of an atherosclerotic plaque. In this particular case, platelets actually respond appropriately to signals they are receiving, but they do so in an inappropriate place.

In autbimmune disease, signaling molecules produced by the processing and presentation of self-antigens activate cells of the immune system, and the activated immune cells respond by eliminating the offensive stimulus. Cells in the body that express the self-antigen are targeted for destruction, and once the function of these normal cells is compromised, symptoms of the autoimmune disease become evident.

Since the pathogenesis of many diseases can be traced to a dysfunction in intercellular signaling, compounds which modulate the signal pathway can have utility in the treatment of a variety of such diseases.

Pheromones are a class of chemicals that are communicative between animals of the same species and elicit stereotypical behavior and endocrine responses. Although there is a wide variety and a large number of pheromone chemical structures, a single pheromone molecule has been shown to have biological effects in non-associated species such as a species of insects and elephants. Some chemical similarities exist between pheromones at different species.

The term "invertebrate pheromone" (or "pheromone") in the context of the present invention should be understood as encompassing any chemical compound isolated from any invertebrate species which is produced and discharged from glands and external ducts and functions by influencing other members of the same species in one of the ways known in the art, and which possesses mitogen-activating protein (MAP) kinase modulation activity. One example of an invertebrate order are insects, one of the predominant species of insects being Lepidoptera.

The terms "pheromone" or "pheromone compound" encompasses the natural pheromones as well as synthetic compounds which display a similar MAP kinase modulating activity. Such synthetic compounds include various derivatives of the natural pheromones, as well as analogs thereof.

The pheromone communication system involves the release of specific chemicals from a pheromone producer (emitter), the transmission of these chemicals in the environment to a receiver, and the processing of the signals to mediate the appropriate behavioral responses in the receiver. Some pheromone compounds are believed to activate the vomeronasal organ (VNO) which resides interior to the main olfactory epithelium (MOE) in a blind-ended pouch within the septum of the nose. In both locations, the VNO and MOE neuroepithelial dendrites terminate in specialized cilia containing specific receptors that bind odorants. This binding initiates a cascade of enzymatic reactions that results in the production of messengers and the eventual depolarization of the cell membrane.

The signal transduction mechanisms through which pheromone compounds exert their effect involve various pathways which are commonly found in various other biological processes.

Applicants have investigated pheromone compounds as a class of chemicals that have potential modulating activity for the MAP kinase signal transduction pathway. The potential of active pheromone compounds to modulate (i.e. activate or inhibit) the MAP kinase signal transduction pathways provides compounds which may be used for the treatment of a wide variety of diseases, conditions, and symptoms thereof as mentioned above. For example, MAP kinase pathway inhibitors have been described 20 as effective in treating cancer and other proliferative diseases such as psoriasis and restenosis as disclosed in A. J. Bridges et al., U.S. Pat. No. 5,525,625. MAP kinase pathway inhibitors have also been described as being effective in abolishing resistance to myocardial infarction induced by heat stress in M. Joyeux et al., Cardiovasc. Drugs Ther., Vol.14/3, pp.337–343 (June, 2000). It is also known that MAP kinase pathway activators can desirably affect wound healing and tissue repair.

It would therefore be a significant advance in the art of treating diseases, conditions and symptoms thereof to identify pheromone compounds possessing MAP kinase modulating activity. It would also be a further advance in the art to identify pheromone compounds which have MAP kinase modulating activity because of their potential for use in treating a variety of diseases, conditions, and symptoms thereof including cancer, autoimmune disease, psoriasis, restenosis as well as wound healing and tissue repair resulting from physical causes including, but not limited to, medical treatment such as chemotherapy. It would be a further advance in the art if pheromone compounds having MAP kinase modulating activity could be effectively identified from a library of pheromone compounds.

SUMMARY OF THE INVENTION

The present invention is generally directed to the discovery that certain pheromone compounds possess mitogen-activated protein (MAP) kinase modulating activity. In one aspect of the present invention, there is provided a screening method for identifying compounds having MAP kinase modulating activity from a library of pheromone compounds. In a further aspect of the invention there is provided pharmaceutical compositions containing as an active agent at least one MAP kinase modulator. Such composition have potential for use in the treatment of a variety of diseases, conditions, and symptoms thereof.

In a first aspect of the present invention, there is a provided a method of screening compounds to obtain those having mitogen-activated protein (MAP) kinase modulating activity, comprising the steps of:

a) providing a biological model for screening of compounds having MAP kinase modulating activity, the model being predictive for MAP kinase modulating activity;

b) testing a group of invertebrate-derived non-peptide, non-steroid pheromone compounds in the biological model to determine the presence of MAP kinase modulating activity; and c) selecting at least one of the pheromone compounds possessing MAP kinase modulating activity in the model to obtain at least one selected pheromone compound.

In another aspect of the present invention, there is a method of selecting compounds having MAP kinase modulating activity, comprising the steps of:

a) providing data relating to the three-dimensional (3D) structure of at least one pharmacophore of a compound known to possess MAP kinase modulating activity;

b) providing a library of compounds, the library comprising at least one pheromone compound selected from invertebrate-derived, non-peptide, and non-steroid pheromones; and c) analyzing the 3D structure of one or more compounds of the library and selecting a compound having a domain with a 3D structure at least substantially similar to the 3D structure of the pharmacophore.

Optionally, the above selection method further comprises the step of testing a selected compound in a relevant biological model which is predictive of the desired MAP kinase modulating activity.

In a further aspect of the present invention, there is provided a pharmaceutical composition comprising an effective amount of at least one invertebrate derived, non-peptide, non-steroid pheromone compound or derivative thereof having mitogen-activated protein kinase modulating activity in combination with a pharmaceutically acceptable carrier. Methods of using the compositions to modulate mitogen-activated protein kinase signal transduction pathways is also encompassed by the present invention.

DETAILED DESCRIPTION OF THE INVENTION

In accordance with the present invention it has been discovered that certain pheromone compounds, derivatives and analogs thereof (hereinafter "pheromone compounds") possess MAP kinase modulating activity and that such pheromone compounds are a source of pharmaceutical agents which may be used for preventing and/or treating diseases, conditions or symptoms thereof. Compounds of the present invention having potential pharmaceutical activity may be selected first on their ability to modulate MAP kinase activity in the associated signal transduction pathway. Such target compounds may be screened from a library of pheromone compounds to provide compounds having the desired pharmaceutical uses which involve MAP kinase activity. "Modulating activity" is defined herein as activity which either activates, inhibits or otherwise varies the action of MAP kinase and/or the corresponding enzyme cascade along the MAP kinase signal transduction pathway. The selection of compounds which either increases or slows the action of MAP kinase and/or corresponding enzyme cascade along the MAP kinase signal transduction pathway, may be carried out using known assays in the art. Alternatively, it may also be possible, in accordance with the present invention, to separately screen compounds which increases or activates the MAP kinase activity in the associated signal transduction pathway, and to separately screen compounds which cause a slowing or inhibiting effect on the MAP kinase activity using a separate assay. In addition, compounds of the present invention may be selected directly which are useful in indications known to involve MAP kinase signal transduction pathway.

"Activators" as used herein include pheromone compounds which increase or activate MAP kinase activity and/or a corresponding enzyme cascade of the MAP kinase signal transduction pathway.

"Inhibitors" as used herein include pheromone compounds which slow or inhibit MAP kinase activity and/or the corresponding enzyme cascade of the MAP kinase signal transduction pathway.

The term "therapeutic activity" is defined herein as any activity of a compound on specific target cells, tissue or organ, or activity which achieves a specific effect within a body including prevention and/or treatment of a disease, condition or symptom thereof, associated with or related to MAP kinase signal transduction pathway in warm-blooded animals including humans. The term "therapeutic activity" is further defined as any activity which is manifested in relatively low levels or concentration of the active compound, which is a concentration which gives rise to a biological effect within the body, not through a general systemic effect, but rather through a specific effect on specific targets within the body especially those responsive to modulation of the MAP kinase signal transduction pathway.

When the compounds are first selected on the basis of their ability to modulate MAP kinase activity, the selection may be carried out using one or more assays known in the art.

A biological model suitable for screening pheromone compounds for MAP kinase modulation activity may be based on a model which is known and acceptable in the literature for screening of such compounds to select those which have the desired activity. In some indications, the acceptable models are in vitro models, e.g. models involving testing of the effect of the compound on a cell or tissue culture. In other indications, a relevant model having a predictive value is an in vivo model involving laboratory animals, which may include rodents such as rats, mice or rabbits; xenograft models, e.g. an immune-compromised mouse carrying human tissue; and higher order animals such as cats, dogs and even primates. Furthermore, the relevant model may at times be a combination of in vitro and in vivo models, or a combination of several in vitro and/or several in vivo models. In addition, at times the relevant model may also be a model of non-living material such as a model of isolated membranes, a variety of biochemical assays, and the like.

In a preferred screening method, as set forth in Example 1 herein, pheromone compounds with MAP kinase modulating activity are identified using Rat1 cells grown in cell culture dishes. Samples of the pheromone compound are added to respective cell culture dishes containing the Rat1 cells and incubated. A control group is established by treating a separate group of cell culture dishes containing Rat1 cells with the same solutions absent the pheromone compound. After incubation, the Rat1 cells are stimulated with epidermal growth factor to stimulate MAP kinase activation in the Rat1 cells. Upon completion of the incubation period, the Rat1 cells in each of the culture dishes are separately processed to obtain the corresponding cell extract containing proteins indicative of active kinase. The proteins are then separated using known electrophoresis techniques and prepared as a blot for the detection and measurement of active MAP kinase. The resulting blot is analyzed using densitometric techniques to measure the corresponding activity of the tested pheromone compound. The results obtained are compared to the results obtained for the control to measure modulation of the active MAP kinase initially induced by EGF.

A pheromone compound having the desired MAP kinase modulating activity may be selected on the basis of its three dimensional (3D) molecular structure. The term "pharmacophore" is used herein as the structural domain of a compound which is associated with or related to a desired pharmaceutical or biochemical activity. In this manner, the structure of compound having a known pharmaceutical activity may be used as a structural template for efficiently selecting compounds having potentially similar pharmaceutical activity. Once the compounds are selected based on their molecular structure, the selected compounds are tested in the relevant biological model as described above, to determine the presence of the desired pharmaceutical activity.

In accordance with the method described above, the following compounds have been observed to possess mitogen-activating protein kinase modulation activity. MAP kinase activators include cis-7-tetradecenal, cis-7-tetradecenol, cis-7-dodecenyl ester, heneicosene-11-one, cis-6-heneicosene-11-one, cis4-tridecenyl ester, cis4-tridecen-1-yl ester, 2-heptanone, cis-7-tetradecenyl ester, trans-5-decenyl ester, cis-2-methyl-7-octadecene, cis-9-heneicosene, trans-2, cis-13-octadecadienal, 14-methyl-cis-8-hexadecenal, 2-methyl-3-butene-2-ol, trans-10-dodecenol, cis-9-tetradecenyl-formate, cis-9-tetradecenol, trans-3, cis-8, cis-11-tetradecatrienol, cis-7-tridecenol, cis-9-pentadecenol, and cis-9-undecenyl ester. Applicants have also discovered mitogen-activated protein kinase inhibitors, namely, trans-3, cis-7-tetradecadienyl ester and trans-3, cis-8-tetradecadienyl ester. The ester of the above-identified compounds may be any ester, preferably an acetate.

The above-identified compounds were screened in accordance with the methods described above and thereby demonstrated the desired MAP kinase inhibitory or activating activity.

The non-peptide, non-steroid invertebrate-derived pheromones of the invention may be isolated from an invertebrate by any one of the methods known in the art. Alternatively, the pheromone compound of the present invention may also be chemically synthesized such as disclosed in U.S. Pat. No. 5,728,376 incorporated herein by reference. Many of the invertebrate pheromone compounds including insect-derived pheromone compounds may be synthesized through the fatty acid synthesis pathway.

The invertebrate-derived pheromone compounds of the present invention have a molecular weight typically less than about 500 Daltons, and more typically less than about 300 Daltons.

Typically, the pheromone compound comprises a straight or branched hydrocarbon chain of variable length (typically having a length of from about 6 to 30 carbon atoms, preferably from about 7 carbon atoms to 23 carbon atoms, more preferably from about 9 carbon atoms to 21 carbon atoms). The hydrocarbon chain may comprise one or more double or triple bonds which may be located at any position in the chain, the double bonds being in the cis or trans configuration. Typically, the side chains in a branched main hydrocarbon chain may include alkyl groups, alkenyl groups, and/or alkynyl groups, each side chain comprising from one to five carbon atoms. The main hydrocarbon chain may also comprise or be linked to a cycloalkyl or cycloalkenyl group having from about 3 to 7 carbon atoms.

The main hydrocarbon chain may be substituted at any location of the chain by one or more functional groups including, for example, a hydroxyl, a ketone, an aldehyde, an epoxy group, a carboxylic acid, an ester, a heterocyclic group, and an aromatic group.

In addition, the hydrocarbon chain of the pheromone compound may also comprise one or more additional groups which may, for example, be selected from ketones, halides (such as for example, F, Cl, Br, I), acetate esters, amines, thiols, thioesters, short chain alkyls (such as for example, methyl, ethyl, propyl, butyl, pentyl).

All of the above modifications may be carried out by known techniques utilized by one of ordinary skill in the art.

In accordance with the invention compounds which comprise modified functional groups in which, for example, an oxygen atom is replaced by a sulfur atom, may also be used and fall within the meaning of the term "pheromone compound" as used herein. Thus, for example, a hydroxyl may be replaced by a thiol, an ester or a thioester. Another example of a modification may be the replacement of a hydrogen atom by a halogen atom, such as, for example, a bromine atom. All of the above modifications may be carried out by known techniques utilized by one of ordinary skill in the art.

In accordance with the invention, derivatives or analogs of the invertebrate pheromone compound may also be used if they substantially maintain the MAP kinase modulating activity of the parent pheromone compound. The activity includes the desirable preventive or therapeutic activity of the pheromone compounds observed to modulate MAP kinase activity along the MAP kinase signal transduction pathway.

A "derivative or analog" of a pheromone compound as used herein includes any compound having the basic structure of the invertebrate pheromone in which one or more functional groups are modified, but which substantially maintains the desired activity of the unmodified pheromone. Such derivative or analog may include geometric isomers of the corresponding pheromone compound having the same or similar level of MAP kinase modulating activity.

A derivative or analog which "substantially maintains" the activity of the unmodified pheromone, includes those displaying MAP kinase modulating activity of a magnitude of at least 30%, preferably at least 50% of the activity of the unmodified pheromone. Where the end biological effect of the pheromone compound includes the prevention and/or treatment of a disease, condition or symptom, a derivative or analog of the pheromone compound may be regarded as substantially maintaining the MAP kinase modulating activity, if it achieves a similar preventive or therapeutic effect at a non-toxic concentration.

It will be understood that at times, the modification of a pheromone compound to form a derivative or analog thereof, may achieve the desired therapeutic activity at the same time may result in the loss or alteration of one or more inherent properties associated with the unmodified pheromone compound.

The invention further provides a pharmaceutical composition suitable for administration to a warm-blooded animal including humans, comprising as an active agent an effective amount of a pheromone compound as defined herein having a desired therapeutic activity associated with the modulation of MAP kinase activity, and a pharmaceutically acceptable carrier.

The term "effective amount" as used herein includes an amount of the active pheromone compound which provides a desirable preventive or therapeutic effect in a warm-blooded animal including human afflicted with a disease, condition or symptom related to MAP kinase activity in the MAP kinase signal transduction pathway. It will be understood that the effective amount will depend on various factors such as, for example, the nature of the indication for which the agent is used, characteristics of the treated warm-blooded animal, and mode of administration and the like, and will be routinely determined by one of ordinary skill in the art.

The effective amount of the pheromone compound will typically be in the range of from about 0.001 to 200 mg/kg/day, preferably from about 0.01 to 20 mg/kg/day.

The pharmaceutical composition comprising at least one pheromone compound having MAP kinase modulating activity may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those known in the art of pharmaceutical formulation.

The present invention further provides a method of treating warm-blooded animals including humans afflicted with a disease, condition, or symptoms which may benefit from modulation of MAP kinase activity comprising administering to the warm-blooded animal an effective amount of a pheromone compound being selected from one or more suitable screening methods disclosed herein and those that may be known in the art.

For use in the methods of the present invention associated with the prevention and/or treatment of diseases, conditions, and symptoms thereof, the pheromone compound may be administered to a warm-blooded animal including humans by one of a variety of administration modes, including, but not limited to oral, intravenous, intramuscular, transdermal, subcutaneous, topical, sublingual, rectal means, by nasal application, and the like. In addition, the pheromone compound may be a volatile substance and thus has the advantage of being administered by inhalation, resulting, in many cases in a very rapid response to the active agent with relatively little, if any, side effects.

When the pheromone compound of the present invention is administered orally, it may be administered in the form of a tablet, a pill, a capsule (e.g. a gelatin capsule), a powder or a pellet. Where a liquid carrier is used, the oral preparation may be in the form of a syrup, emulsion, or soft gelatin capsule. Nasal administration may be by nasal insufflation or as an aerosol, and internal administration such as rectal administration may be, for example, by use of a suppository. For topical administration the pheromone compounds may be, for example, in the form of creams, ointments, lotions, solutions, gels or transdermal patches.

The pheromone compounds of the invention may typically be administered with a pharmaceutically acceptable carrier which does not interfere with the efficacy of the active pheromone compound. The carrier may be selected from a large number of carriers known in the art and the nature of the carrier will depend on the intended form of administration and indication for which the active agent is used.

Tablets, pills and capsules containing the pheromone compounds of the invention may also include conventional excipients such as lactose, starch, and magnesium stearate. Suppositories may include excipients such as waxes and glycerol. Injectable solutions may comprise saline, buffering agents, dextrose, water glycerol, ethanol and solvents such as propylene glycol, polyethylene glycol and ethanol. Such solutions may also comprise stabilizing agents and preservatives which are typically antimicrobial agents (such as chlorbutol, benzyl alcohol, sodium benzoate, ascorbic acid, phenol, and the like) and antioxidants (such as butylated hydroxy toluene, propyl gallate, sulfites, and the like). Enteric coatings, flavorings, and dyes and colorants may also be used.

At times, the pheromone compounds of the invention may be incorporated within a liposome prepared by any of the methods known in the art. In addition, the pheromone compounds may be encapsulated in inert polymerized particles such as, for example, nano particles, microspheres, microparticles, and the like known in the art.

The pheromone compounds of the invention may comprise a single active agent or alternatively two or more such active agents which may exert an enhanced effect.

According to the methods of administration as encompassed by the present invention, the pheromone compounds may be administered separately or, alternatively, in combination with various other treatments administered to the patient for the same or different disease, condition, or symptom thereof.

The foregoing discussion discloses and describes merely exemplary embodiments of the present invention. One skilled in the art will readily recognize from such discussion, and from the examples which follow, and from the claims, that various changes, modifications, and variations can be made therein without departing from the spirit and scope of the invention.

The following examples are submitted for illustrative purposes only and are not intended to limit the invention as encompassed by the claims forming part of the application.

EXAMPLE 1

Screening Method For The Identification Of Pheromone Compounds Having MAP Kinase Modulating Activity Rat1 cells were grown in 6 cm cell culture dishes in a tissue culture incubator at 37° C. in an atmosphere containing 5% carbon dioxide. The cells were serum-starved for 16 hours. A solution containing from about 5 to 500 ng/ml of a pheromone compound which may be a MAP kinase activator, inhibitor, or a compound which exhibits no MAP kinase modulation activity, was added to the cell culture dishes and allowed to stand for about 15 minutes. A control group was established by adding to the remaining cell culture dishes the same solution absent the pheromone compound. After the 15 minute period, the Rat1 cells were stimulated with epidermal growth factor (EGF) (50 ng/ml) for about 15 minutes for one group and 30 minutes for a second group.

The Rat1 cells were then treated to remove the corresponding incubation medium and then the cells were rinsed twice each with 5 ml of cold phosphate buffered saline (PBS) and once with 5 ml of cold homogenizing buffer (Buffer H) containing 50 mM of β-glycerophosphate, (pH 7.3), 1.5 mM of ethylenebis(oxyethylenenitrilo)tetraacetic acid (EGTA), 1 mM of ethylenediaminetetraacetic acid (EDTA), 1 mM of dithiothreitol (DTT), 0.1 mM sodium orthovanadate, 1 mM benzamidine, 10 µg/ml of aprotinin, 10 µg/ml of leupeptin, and 2 µg/ml of pepstatin (2 µg/ml)+ 1% Triton-X-100.

The cells were harvested and lysed with 350 µl of cold Buffer H. Alternatively, the cells may be harvested and lysed with radioimmunoprotein assay buffer (RIPA buffer). Each extract was then centrifuged at 15,000×g for 15 minutes at 4° C. The resulting supernatants contained the protein extracts to be examined and were transferred to fresh, pre-cooled test tubes and kept on ice.

The proteins were then separated by sodium dodecyl sulfate-polyacrylamide gel electrophoresis (SDS-PAGE) and transferred, by western blotting, onto a nitrocellulose membrane.

The blot produced above was blocked with 2% bovine serum albumin (BSA) in Tris-buffered saline/Tween-20 (TBST) for 1 hour. The blot was then incubated with a monoclonal anti-active MAP kinase antibody obtained from Sigma, and diluted according to the manufacturer recommendations. The blot was incubated overnight at 4° C. Alternatively, the blot may also be incubated for about 30 minutes at 37° C., or from one to two hours at room temperature.

The treated blot was placed in a flat container and washed at least 3 times for 15 minutes each with TBST buffer at room temperature. The blot was then incubated with alkaline phosphatase-conjugated goat anti-mouse IgG obtained from Jackson Laboratories, diluted according to the manufacturer recommendations in TBST buffer for 45 minutes at room temperature. The blot was then subjected to a second washing, repeated 3 times, for 10 minutes each with TBST. An alkaline phosphatase (AP) detection technique was utilized to detect and measure the presence of active MAP kinase. Enhanced MAP kinase activity as compared to control is evidence that the compound is a MAP kinase activator. Lowered MAP kinase activity as compared to control is evidence that the compound is a MAP kinase inhibitor. Unchanged MAP kinase activity as compared to control is evidence that the compound is neither an activator nor an inhibitor of MAP kinase.

EXAMPLE 2

Demonstration of Pheromone Compounds Having MAP Kinase Inhibiting Activity

Rat1 cells grown in a series of cell culture dishes were prepared in the same manner described above in Example 1. The cells were serum-starved for 16 hours. Three groups of cell culture dishes containing Rat1 cells were each preincubated for about 30 minutes with solution containing the pheromone compound, trans-3, cis-7-tetradecadienyl-acetate at a concentration of $10^{-4}$ M, with a solution containing the pheromone compound, trans-3, cis-8-tetradecadienyl-acetate at a concentration of $10^{-4}$ M, or a control solution absent any pheromone compound. After preincubation, all of the Rat1 cells were stimulated with epidermal growth factor (EGF) (25 ng/ml) for about 15 minutes for one group and 30 minutes for a second group. The Rat1 cells were then washed with phosphate buffered saline (PBS) and lysed with RIPA buffer. The proteins were then separated by sodium dodecyl sulfate-polyacrylamide gel electrophoresis (SDS-PAGE) and probed with anti-active-MAPK antibodies. The inhibitory effect of the pheromone compound on MAPK activity was calculated as the percent EGF-induced activity as indicated by densitometry analysis as compared to the control receiving no pheromone compound. The results are presented in Table 1 below.

TABLE 1

| Pheromone Compounds | Inhibition of MAP Kinase activity (% of Control) | |
| --- | --- | --- |
| | 15 minute activation by EGF | 30 minute activation by EGF |
| Trans-3,Cis-7-Tetradecadienyl-acetate | 75% | 85% |
| Trans-3,Cis-8-Tetradecadienyl-acetate | 50% | X |

X - not available

As shown in Table 1 the pheromone compounds significantly inhibited EGF-stimulated kinase activity as compared with the control.

EXAMPLE 3

Demonstration of Pheromone Compounds Having MAP Kinase Activating Activity Compared to Known Activating Agents of MAP Kinase Rat1 cells were grown in 6 cm cell culture dishes in a tissue culture incubator at 37° C. in an atmosphere containing 5% carbon dioxide. The Rat1 cells were serum-starved for 16 hours. Three groups of the Rat1 cells were then treated for 15 minutes with either epidermal growth factor (EGF) (50 ng/ml), 12-O-tetradecanoylphorbol-13-acetate (TPA) (100nM), or with one of the pheromone compounds at one of two concentrations identified in Table 2 below. EGF and TPA are compounds which are known to activate MAP kinase and therefore serve as a basis of comparing the relative activity of the pheromone compounds. The cells were then washed with phosphate buffered saline (PBS) and lysed with radioimmunoprotein assay (RIPA) buffer. The proteins were then separated by sodium dodecyl sulfate-polyacrylamide gel electrophoresis (SDS-PAGE), transferred onto a nitrocellulose membrane and probed with anti-MAPK antibodies to produce a blot. The MAP kinase activity for the EGF-treated cells, the TPA-treated cells and the pheromone compound-treated cells, was analyzed and calculated using densitometric analysis. The results shown in Table 2 are presented as percent of EGF-stimulated active MAP kinase levels or TPA-stimulated active MAP kinase levels, respectively. For example, at a concentration of 1×10-4 M, cis-7-tetradecenal, showed an MAP kinase activation that was 7% of the MAP kinase activation detected in rat cells stimulated by EGF.

TABLE 2

| Pheromone Compounds | Activity (% of EGF-activation) | | Activity (% of TPA-activation) | |
|---|---|---|---|---|
| | Conc. 1 (1 × $10^{-4}$ M) | Conc. 2 (1 × $10^{-5}$ M) | Conc. 1 (1 × $10^{-4}$ M) | Conc. 2 (1 × $10^{-5}$ M) |
| Cis-7-Tetradecenal | 7 | 5 | 20 | 10 |
| Cis-7-Tetradecenol | 9 | 9 | 30 | 25 |
| Cis-7-Dodecenyl-acetate | 7 | 8 | 20 | 17 |
| Heneicosene-11-one | 12 | 12 | 42 | 22 |
| Cis-4-Tridecen-1-yl-acetate | 3 | 5 | 7 | 30 |
| 2-Heptanone | 5 | 7 | 14 | 50 |
| Cis-7-Tetradecenyl-acetate | 8 | 10 | 21 | 80 |
| Trans-5-decenyl-acetate | 1 | 4 | X | 18 |
| Cis-2-methyl-7-Octadecene | 8 | 8 | 60 | 45 |
| Cis-9-Heneicosene | X | 3 | X | 22 |
| Trans-2,Cis-13-Octadecadienal | 4 | 8 | 30 | 40 |
| 14-methyl-Cis-8-Hexadecenal | 10 | 3 | 75 | 15 |
| 2-methyl-3-butene-2-ol | 5 | X | 35 | X |
| Trans-10-Dodecenol | 2 | 10 | 10 | 60 |
| Cis-9-Tetradecenyl-formate | 12 | 12 | 90 | 55 |
| Cis-9-Tetradecenol | 15 | 8 | 105 | 35 |
| Trans-3,Cis-8,Cis-11-Tetradecatrienol | 6 | 5 | 10 | 50 |
| Cis-7-Tridecenol | 12 | 9 | 80 | 60 |
| Cis-9-Pentadecenol | 14 | 6 | 95 | 30 |
| Cis-9-Undecenyl-acetate | 18 | 3 | 115 | 10 |

X-not available

As shown in Table 2, each of the pheromone compounds tested exhibited increased MAP kinase activity as compared with EGF or TPA.

EXAMPLE 4

Formulation Containing Pheromone Compounds of the Present Invention Suitable for Parenteral Administration 4.5 grams (g) of beta-hydroxypropylcyclodextrin (beta-HPCD) were added to 5.5 g of purified water and mixed together until the beta-HPCD was completely dissolved and a clear viscous solution was formed. 5 mg of a pheromone compound (e.g. cis-7-tetradecenal, or cis-7-tetradecenol, or trans-3, cis-7-tetradecadienyl acetate) of the present invention was added to the prepared HPCD solution and mixed under heating at 65–70° C. until the pheromone compound was completely dissolved. The resulting solution was passed through a nylon membrane filter having a pore size of about 0.45 micron. The filtered solution was then allowed to cool. The thus prepared solution was diluted to a desired concentration using 45% water solution of HPCD.

EXAMPLE 5

Formulation Containing Pheromone Compounds of the Present Invention Suitable for Parenteral Administration 50 mg of hexadecanol was melted with 950 mg of Tween-80 in a water bath. The composition was then allowed to cool. Upon cooling, the gel-like composition was dissolved and an amount of a pheromone compound (e.g. cis-7-tetradecenal, or cis-7-tetradecenol, or trans-3, cis-7-tetradecadienyl acetate) of the present invention was dissolved into 99 ml of warm purified water. A transparent micellar solution was thus formed suitable for parenteral administration.

EXAMPLE 6

Formulation Containing Pheromone Compounds of the Present Invention Suitable for Parenteral Administration A microemulsion composition was prepared by mixing 1800 mg of Tween-80, a non-ionic surfactant with 1500 mg of medium chain triglycerides oil (CRODAMOL™ TGCC). 100 mg of a pheromone compound (e.g. cis-7-tetradecenal, or cis-7-tetradecenol, or trans-3, cis-7-tetradecadienyl acetate) of the present invention was dissolved into the surfactant-oil mixture under slight heating at 45–50° C. Optionally, 200 mg of a cosolvent such as enthoxydiglycol (TRANSCUTOL™, Gattefosse, France) may be added for improved stability. The resulting solution was filtered through a 0.22 micron membrane filter for sterility and the resulting solution was suitable for parenteral injection.

EXAMPLE 7

Formulation Containing Pheromone Compounds of the Present Invention Suitable for Parenteral Administration A microemulsion composition was prepared by mixing 3600 mg of Tween-80, a non-ionic surfactant with 2700 mg of medium chain triglycerides oil (CRODAMOL™ TGCC). 100 mg of a pheromone compound (e.g. cis-7-tetradecenal, or cis-7-tetradecenol, or trans-3,cis-7-tetradecadienyl acetate) of the present invention was dissolved into the surfactant-oil mixture under slight heating at 45–50° C. Upon cooling, 300 mg glycol laurate (LABRASOL™) was added to the final solution and mixed thoroughly until dissolved. The solution was then filtered through a 0.22 micron membrane filter for sterility and the resulting solution was suitable for parenteral injection.

EXAMPLE 8

Formulation Containing Pheromone Compounds of the Present Invention Suitable for Oral Administration 400 mg of a pheromone compound (e.g. cis-7-tetradecenal, or cis-7-tetradecenol, or trans-3, cis-7-tetradecadienyl acetate) of the present invention was admixed with 1.0 g of polyvinylpyrrolidone (PVP K-25™, BASF). The admixture was dissolved in 20 ml of ethyl alcohol USP grade. The resulting solution was used for granulation of a mixture of 4.6 g of dibasic calcium phosphate dihydrate (EMCOPRESS™, Mendell Co.) and 5.9 g of microcrystalline cellulose (AVICEL® pH102, FMC). The resulting granulation was dried at 45° C. and passed through a stainless steel sieve (#16 mesh). The sieved granules were mixed with 0.1 g of magnesium stearate. 900 mg of the final granulation was encapsulated in a size 00 hard gelatin capsule, providing 30 mg of the pheromone compound per capsule.

EXAMPLE 9

Formulation Containing Pheromone Compounds of the Present Invention Suitable for Oral Administration 400 mg of a pheromone compound (e.g. cis-7-tetradecenal, or cis-7-tetradecenol, or trans-3, cis-7-tetradecadienyl acetate) of the present invention was admixed with 2.0 g of isopropyl palmitate, 4 g of MIRJ®-52 (PEG-40 stearate, USP/NF grade), and 1.0 g of polyvinylpyrrolidone (PVP K-25™, BASF). The admixture was dissolved in 30 ml of ethyl alcohol USP grade. The resulting solution was used for granulation of a mixture of 5.6 g of calcium silicate (HIPERSORB™, Daminco) and 1.9 g of dibasic calcium phosphate dihydrate (EMCOPRESS™, Mendell Co.). The resulting granulation was dried at 45° C. and passed through a stainless steel sieve (#16 mesh). The sieved granules were mixed with 0.1 9 of magnesium stearate. 750 mg of the final granulation was encapsulated in

EXAMPLE 10

Formulation Containing Pheromone Compounds of the Present Invention Suitable for Suppository Use 125 mg of a pheromone compound (e.g. cis-7-tetradecenal, or cis-7-tetradecenol, or trans-3, cis-7-tetradecadienyl acetate) of the present invention was melted with 3.6 g of a suppository base comprising cacao butter (99.6%) and butylated hydroxytoluene (0.4%). The melted composition was mixed well with a spatula and then molded into four oval suppositoria using a suitable mold. Weighing 960 mg each, with suppositoria containing about 30 mg of the pheromone compound.

EXAMPLE 11

Formulation Containing Pheromone Compounds of the Present Invention Suitable for Topical Administration An ointment comprising 5% a pheromone compound (e.g. cis-7-tetradecenal, or cis-7-tetradecenol, or trans-3, cis-7-tetradecadienyl acetate) of the present invention was prepared by mixing 500 mg of the pheromone compound with 7.5 g of white petrolatum, 0.5 g lanolin and 1.5 g of POLAWAX™(Emulsifying wax NF grade, Croda). The resulting mixture was further mixed until cooling which resulted in an oleaginous ointment.

EXAMPLE 12

Formulation Containing Pheromone Compounds of the Present Invention Suitable for Topical Administration A water-in-oil emulsion cream containing 1% of a pheromone compound (e.g. cis-7-tetradecenal, or cis-7-tetradecenol, or trans-3, cis-7-tetradecadienyl acetate) of the present invention was prepared by dissolving 1 g of pheromone compounds in a mixture of 20 g of isopropyl palmitate and 10 g of POLAWAX™(Emulsifying wax NF grade, Croda) at 70° C. to form a lipid phase. A water phase comprising 66 g of purified water, 2.5 g of glycerin and 0.5 g of phenoxyethanol was heated to 70° C., then slowly added to the lipid phase, and vigorously mixed while cooling. Upon cooling, a stable cream was obtained and packaged in an airtight container.

EXAMPLE 13

Formulation Containing Pheromone Compounds of the Present Invention Suitable for Topical Administration A clear gel preparation containing 0.5% of a pheromone compound (e.g. cis-7-tetradecenal, or cis-7-tetradecenol, or trans-3, cis-7-tetradecadienyl acetate) of the present invention was prepared by slowly adding 2.5 g of hydroxypropylcellulose (Klucel HF) to 37.0 g of purified water. The solution was heated to 70° C. The heated solution was mixed while allowing the temperature to fall to room temperature resulting in a viscous gel as a water phase. Separately, 0.5 g of the pheromone compound of the present invention was dissolved in a mixture of 40 g ethoxydiglycol (TRANSCUTOL™), 10 g of isopropyl myristate, and 10 g of PLURONIC™ F-127 to form an organic phase. The water and organic phases were combined and slowly mixed until a uniform composition was obtained. After degassing for 24 hours, a smooth clear gel was formed.

What is claimed is:

1. A method of treating a warm-blooded animal afflicted with a disease selected from the group consisting of cancer, inflammation, neurodegenerative diseases, neurological diseases, autoimmune diseases, allergy related diseases and hormone related diseases, restenosis, psoriasis, myocardial infarction, wounds and tissue repair and conditions and symptoms thereof that would benefit from modulation of MAP kinase activity, comprising administering to the warm-blooded animal a MAP kinase modulating effective amount of a pheromone compound selected from the group consisting of cis-7-tetradecenal, cis-7-tetradecenol, cis-7-dodecenyl ester, heneicosene-11-one, cis-6-heneicosene-11- one, cis4-tridecenyl ester, cis4-tridecen-1-yl ester, 2-heptanone, cis-7-tetradecenyl ester, trans-5-decenyl ester, cis-2-methyl-7-octadecene, cis-9-heneicosene, trans-2, cis-13-octadecadienal, 14-methyl-cis-8-hexadecenal, 2-methyl-3-butene-2-ol, trans-10-dodecenol, cis-9-tetradecenol, cis-9-tetradecenyl-formate, cis-9-tetradecenol, trans-3, cis-8, cis-11 -tetradecatrienol, cis-7-tridecenol, cis-9-pentadecenol, cis-9-undecenyl ester, trans-3, cis-7-tetradecadienyl ester, trans-3, cis-8-tetradecadienyl ester, and derivatives and analogs thereof.

2. The method of claim 1 wherein the MAP kinase modulating effective amount is from about 0.1 to 200 mg/kg/day.

3. The method of claim 1 wherein the MAP kinase modulating effective amount is from about 2.0 to 180 mg/kg/day.

4. The method of claim 1 wherein the ester is an acetate.

5. The method of claim 1, the pheromone compound inhibits MAP kinase activity, wherein MAP kinase inhibiting compound is selected from the group consisting of trans-3, cis-7-tetradecadienyl ester and trans-3, cis-8-tetradecadienyl ester.

6. The method of claim 1, the pheromone compound activates MAP kinase activty, wherein MAP kinase inhibiting compound is selected from the group consisting of cis7-tetradecenal, cis-7-tetradecenol, cis-7-dodecenyl ester, heneicosene-11-one, cis-6-heneicosene-11-one, cis-4-tridecenyl ester, cis-4-tridecen-1-yl ester, 2-heptanone, cis-7-tetradecenyl ester, trans-5-decenyl ester, cis-2-methyl-7-octadeoene, cis-9-heneicosene, trans-2, cis-13-octadecadienal, 14-methyl-cis-8-hexadecenal, 2-methyl-3-butene-2-ol, trans-10-dodecenol, cis-9-tetradecenyl-formate, cis-9-tetradecenol, trans-3, cis8, cis-11-tetradecatrienol, cis-7-tridecenol, cis-9-pentadecenol, and cis-9-undecenyl ester.

* * * * *

UNITED STATES PATENT AND TRADEMARK OFFICE
CERTIFICATE OF CORRECTION

PATENT NO. : 6,806,293 B1
DATED : October 19, 2004
INVENTOR(S) : Nadav Zamir

It is certified that error appears in the above-identified patent and that said Letters Patent is hereby corrected as shown below:

<u>Column 14,</u>
Line 24, "-one, cis4-tridecenyl ester, cis4-tridecen-1-yl] ester" should read -- -one, cis-4-tridencenyl ester, cis-4-tridecen-1-yl] ester,"
Line 46, delete the word "activates" insert -- inhibits --;
Line 46, delete the word "activty" insert -- activity --;
Line 48, "cis7-tetradecenal," insert -- cis-7-tetradecenal, --;
Line 51, delete the word "octadeoene" insert -- octadecene --; and
Line 54, delete "cis8" insert -- cis-8 --.

Signed and Sealed this

Twenty-second Day of February, 2005

JON W. DUDAS
*Director of the United States Patent and Trademark Office*